United States Patent [19]

Burow, Jr. et al.

[11] 4,452,631

[45] Jun. 5, 1984

[54] UREA HERBICIDES

[75] Inventors: Kenneth W. Burow, Jr., Indianapolis; George W. Johnson, Greenfield, both of Ind.

[73] Assignee: Eli Lilly and Company, Indianapolis, Ind.

[21] Appl. No.: 366,884

[22] Filed: Apr. 8, 1982

Related U.S. Application Data

[63] Continuation-in-part of Ser. No. 280,743, Jul. 6, 1981, abandoned.

[51] Int. Cl.³ ............................................. A01N 47/30
[52] U.S. Cl. ..................................... 71/120; 564/44; 71/90; 71/91; 71/92; 71/93; 71/94; 71/100; 71/103; 71/108; 71/114; 71/115; 71/116; 71/118; 71/121; 71/122; 71/124
[58] Field of Search .................................. 71/120, 118

[56] References Cited

U.S. PATENT DOCUMENTS

| | | | |
|---|---|---|---|
| 3,012,872 | 12/1961 | Richter | 71/118 |
| 3,253,902 | 5/1966 | Münz et al. | 71/120 |
| 3,342,586 | 9/1967 | Lehureau et al. | 71/120 |
| 3,384,473 | 5/1968 | Pillon et al. | 71/120 |
| 3,385,692 | 5/1968 | Knowles | 71/120 |
| 3,518,304 | 6/1970 | Swithenbank et al. | 71/120 |
| 3,734,961 | 5/1973 | Englehart | 71/120 |
| 3,748,356 | 7/1973 | Wellinga et al. | 71/120 |
| 4,166,124 | 8/1979 | Wellinga et al. | 424/273 |

FOREIGN PATENT DOCUMENTS 7105350 10/1972 Netherlands ......................... 71/120

OTHER PUBLICATIONS

Wellinga et al. II, "Synthesis and Laboratory etc;" (1973) J.A.G. Food Chem. 21 pp. 993-998 (1973).

Primary Examiner—Glennon H. Hollrah
Attorney, Agent, or Firm—Joseph A. Jones; Kathleen R. S. Page; Arthur R. Whale

[57] ABSTRACT

Novel 1-(2,6-dialkoxybenzoyl)-3-(substituted phenyl)ureas are disclosed in the present invention. These compounds are useful both alone and in combination with other herbicides for controlling the growth of undesired plants.

6 Claims, No Drawings

UREA HERBICIDES

CROSS REFERENCE TO RELATED APPLICATIONS

This is a continuation-in-part of Ser. No. 280,743, filed July 6, 1981, now abandoned.

BACKGROUND OF THE INVENTION

Methods and substances useful for the control of growth of unwanted vegetation have been the subject of much research for many years. Such control is of great economic benefit in many instances.

The prior art includes a wide variety of benzoylphenylureas possessing insecticidal activity. Wellinga et al., U.S. Pat. No. 4,166,124 and Netherlands Pat. No. 7,105,350, disclose various 1-(2,6-dihalobenzoyl)-3-phenylureas possessing such activity.

There also exists prior art disclosing 1-benzoyl-1-phenylureas useful as herbicides. Pillon et al., U.S. Pat. No. 3,384,473, teach the use of assorted 1-phenyl-1-benzoyl ureas useful as herbicidal agents. Lehureau et al., U.S. Pat. No. 3,342,586, broadly disclose ureas having herbicidal activity, but teach only 1-phenyl-1-alkanoyl ureas as a preferred class of compounds.

SUMMARY OF THE INVENTION

The present invention relates to a compound of the formula

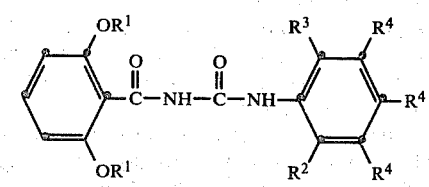

wherein both $R^1$ groups are the same and represent methyl or ethyl; both $R^2$ and $R^3$ represent the same moiety which is methoxy or halogen other than fluorine, and $R^4$ represents hydrogen; or $R^2$ represents fluorine, and both $R^3$ and $R^4$ represent hydrogen; or $R^2$ and $R^3$ both represent fluorine, and $R^4$ represents hydrogen or fluorine.

The present invention also provides a herbicidal method for the use of such novel compounds, as well as compositions containing such compounds.

DETAILED DESCRIPTION OF THE INVENTION

The 2,6-dialkoxybenzoylphenylureas of this invention are prepared by methods currently known in the art. The preferred method of preparation involves reacting a 2,6-dialkoxybenzoyl derivative with anhydrous ammonia to give the corresponding benzamide. The benzamide is then reacted with oxalyl chloride to give a 2,6-dialkoxybenzoylisocyanate, which is finally reacted with an appropriately substituted aniline to give the corresponding 1-(2,6-dialkoxybenzoyl)-3-(substituted phenyl)urea.

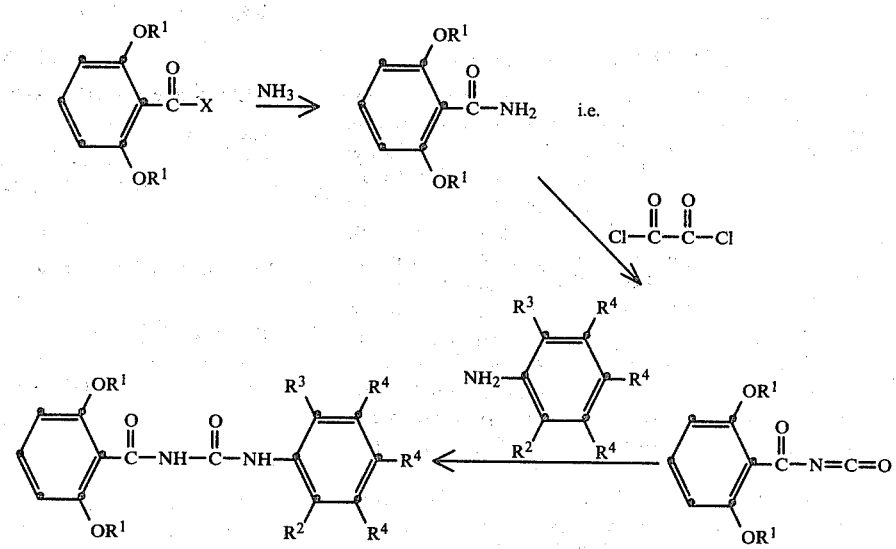

wherein $R^1$, $R^2$, $R^3$ and $R^4$ are as defined above and X is halogen, hydroxy, $C_1$–$C_6$ alkoxy or

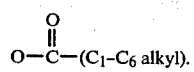

$O-\overset{O}{\overset{\|}{C}}-(C_1-C_6 \text{ alkyl})$.

The final step of the above described reaction is generally performed in a suitable solvent and in an inert atmosphere. The temperature range suitable for addition of the reactants can be from 0° C. to 30° C. with 10° C. to 25° C. being preferred. Suitable solvents include most halogenated solvents with methylene chloride, 1,2-dichloroethane, and chloroform being preferred. Usually following addition of the reactants, the temperature of the reaction mixture is increased from about 20° C. to about 40° C. The reaction is then worked up according to standard procedures. Typically, either the precipitated solid is collected or the solvent removed in vacuo. If the solvent needs to be removed, the resulting product is slurried in a suitable solvent, usually an alcohol, and the solid collected. The product can be further purified by recrystallization or column chromatography.

The substituted aniline and acid chloride starting materials are either commercially available or readily prepared by known methods.

A typical preparation of the starting materials used to prepare compounds of the present invention is represented by the following examples.

2,6-Dimethoxybenzamide

A 200 g. portion of 2,6-dimethoxybenzoyl chloride was added to 2.5 l. diethyl ether and the solution was cooled to 5° C. under nitrogen. The nitrogen was removed and NH$_3$ gas was bubbled through the solution over a two hour period keeping the temperature between 5°–10° C. Stirring was continued for one hour as the temperature was allowed to come to about 25° C.; pH of the solution was 9.0. The solids were filtered and slurried in two liters of water while the pH of the water slurry was adjusted to 8.0 with ammonium hydroxide. The solids were filtered again, washed with water and dried. Yield 167 g. (92%). The material was suitable for use in the next step.

2,6-Dimethoxybenzoylisocyanate

A 167 g. portion of 2,6-dimethoxybenzamide was slurried in 2 l. of toluene under a nitrogen atmosphere. To this solution was added 145 g. of oxalyl chloride over a one hour period. The solution was heated to 60° C. and maintained at this temperature overnight. HCl was allowed to escape while attempting to prevent water from condensing and going into the reaction mixture. Nitrogen was bubbled subsurface through a gas inlet tube while heating the reaction mixture at reflux (about 110° C.) for 1½ hours. As stirring continued, the mixture was allowed to come to about 30° C. The solution was filtered through infusorial earth while maintaining a nitrogen atmosphere and the solvent was removed in vacuo. Yield 185 g. (97%). The oil was then stored under nitrogen.

Starting with the appropriate 2,6-dialkoxybenzoylisocyanate and substituted aniline, compounds of the present invention can be prepared. Typical of these compounds are the following examples:

EXAMPLE 1

1-(2,6-Dimethoxybenzoyl)-3-(2,6-dichlorophenyl)urea

A 16.2 g. portion of 2,6-dichloroaniline (Aldrich Chemical Co., Milwaukee, Wis.) was dissolved in 200 ml. 1,2-dichloroethane in a flask under a nitrogen atmosphere at about 25° C. To this was added 25 g. of 2,6-dimethoxybenzoylisocyanate in 25 ml. 1,2-dichloroethane and the solution was warmed to 40° C. for two hours after the addition was complete. Thin layer chromatography on silica gel developed in diethyl ether indicated that no 2,6-dichloroaniline remained. The solvent was removed in vacuo and the residue slurried in methanol. The solids were collected and washed with methanol. Yield 26.5 g. (72%).

Analysis calculated for $C_{16}H_{14}Cl_2N_2O_4$: Theory: C, 52.02; H, 3.82; N, 7.59; Found: C, 51.81; H, 3.69; N, 7.36.

EXAMPLE 2

1-(2,6-Dimethoxybenzoyl)-3-(2,6-difluorophenyl)urea

A 60 g. portion of 2,6-difluoroaniline was dissolved in 1500 ml. methylene chloride and cooled to 10° C. Under a nitrogen atmosphere, 90 g. of 2,6-dimethoxybenzoylisocyanate in 200 ml. methylene chloride was added dropwise. The mixture was allowed to stir at 25° C. for three hours. The solid was collected and washed with water. The filtrate was evaporated to dryness, and 150 ml. diethyl ether and 150 ml. ethanol were added. The solid was again collected. Yield 89.0 g. (60%).

M.P.=199°–200° C.

Analysis calculated for $C_{16}H_{14}F_2N_2O_4$: Theory: C, 57.15; H, 4.20; N, 8.33; Found: C, 57.20; H, 4.36; N, 8.33.

EXAMPLE 3

1-(2,6-Dimethoxybenzoyl)-3-(2,6-dibromophenyl)urea

M.P.=214°–215° C.

Analysis calculated for $C_{16}H_{14}Br_2N_2O_4$: Theory: C, 41.95; H, 3.08; N, 6.12; Found: C, 41.89; H, 2.93; N, 5.98.

EXAMPLE 4

1-(2,6-Dimethoxybenzoyl)-3-(dimethoxyphenyl)urea

M.P.=208°–210° C.

Analysis calculated for $C_{18}H_{20}N_2O_6$: Theory: C, 59.99; H, 5.59; N, 7.77; Found: C, 59.70; H, 5.39; N, 7.63.

EXAMPLE 5

1-(2,6-Dimethoxybenzoyl)-3-(2-fluorophenyl)urea

M.P.=207°–209° C.

Analysis calculated for $C_{16}H_{15}FN_2O_4$: Theory: C, 60.37; H, 4.75; N, 8.80; Found: C, 60.26; H, 4.67; N, 8.88.

EXAMPLE 6

1-(2,6-Dimethoxybenzoyl)-3-(2,4,6-trifluorophenyl)urea

M.P.=202°–203° C.

Analysis calculated for $C_{16}H_{13}F_3N_2O_4$: Theory: C, 54.24; H, 3.70; N, 7.91; Found: C, 54.50; H, 3.81; N, 8.21.

EXAMPLE 7

1-(2,6-Diethoxybenzoyl)-3-(2,6-difluorophenyl)urea

M.P.=129°–130° C.

Analysis calculated for $C_{18}H_{18}F_2N_2O_4$: Theory: C, 59.34; H, 4.98; N, 7.69; Found: C, 59.08; H, 5.10; N, 7.52.

EXAMPLE 8

1-(2,6-Dimethoxybenzoyl)-3-(2,3,5,6-tetrafluorophenyl)urea

M.P.=183.5°–187° C.

Analysis calculated for $C_{16}H_{12}F_4N_2O_4$: Theory: C, 51.62; H, 3.25; N, 7.53; Found: C, 51.44; H, 3.29; N, 7.64.

The novel compounds of the present invention have been found to display useful pre and postemergent herbicidal activity against a variety of weed species. The compounds may be applied directly to the plants when young, but are preferably applied to the soil prior to the emergence of the plant. The compounds may be either incorporated into the soil, by using a conventional disc or harrow prior to planting the seeds of the desired crop species, or by surface applying the compound to the soil before the plant emergence. In this latter procedure the compounds are merely permitted to leach into the soil with the assistance of rainfall, for example. The compounds of the present invention display activity against a wide variety of weed species, including lambsquarter, pigweed, cocklebur, ragweed, jimsonweed and morningglory, large crabgrass, barnyard grass, mustard, foxtail, wild oat, velvetleaf, zinnia, purslane, prickly sida, fall panicum, devils beggarticks, eclipta, *solanum* spp., blackgrass, catchweed bedstraw, wild chamomile, common chickweed, birdseye speedwell, bristly starbur, southern sanbur, goosegrass, *sida* spp., brazil calalilly, nightshade and a number of other vegetative species which comprise unwanted weed and grass vegetation.

The compounds of the present invention have also been found safe on a wide variety of desirable plant species, thereby exhibiting their unique selective capacity. Representative examples of relatively tolerant plant species, depending on the concentration of active employed, include corn, wheat, rice, barley, soybean, cotton, sorghum, peas, alfalfa, cucumber, tomato, peanuts, sugar beet, rapeseed, cabbage, turnip and the like.

The term "growth inhibiting amount," as defined herein, refers to an amount of a compound of the present invention which either kills or stunts the growth of the weed species for which control is desired. This amount will generally be from about 0.05 to about 15.0 pounds of benzoylphenylurea per acre (about 0.056 to about 16.8 kg./ha.). The compounds are more preferably applied at rates of about 0.25 to about 8.0 pounds per acre (about 0.28 to about 8.96 kg./ha.). The exact concentration of compound required varies with the weed species to be controlled, type of formulation, soil type, climate conditions and the like.

The term "undesired plants," as defined herein, refers to both weeds and weed seeds which are present at the location to be treated with a compound of the present invention. The compounds can be applied to the soil to selectively control undesired plants by soil contact when the weed seeds are germinating and emerging. They can also be used directly to kill emerged weeds by direct contact with the exposed portion of the weed.

The compounds of the present invention may also be formulated with a suitable agriculturallyacceptable carrier. Such compositions will contain from about 0.1 to about 95.0 percent by weight of the active ingredient, depending on the composition desired. Sprayable formulations are preferred, because of the rapidity and economy of application, and because the sprayed applications do not drift to untreated areas as would a dust, for example. Dust compositions containing a compound of the present invention usually contain from about 0.1 to about 10 percent of the compound. Dusts are prepared by intimately mixing and finely grinding the compound with an inert solid such as ground montmorillonite clay, attapulgite clay, talc, ground volcanic rock, kaolin clay, or other inert, relatively dense, inexpensive substances.

The most convenient formulations are in the form of concentrated compositions to be applied by spraying as water dispersions or emulsions containing in the range from about 0.1 percent to about 10 percent of the compounds. Water-dispersible or emulsifiable compositions may be either solids usually known as wettable powders, or liquids usually known as emulsifiable concentrates.

A typical wettable powder comprises an intimate mixture of a compound of the invention, an inert carrier, and surfactants. The concentration of the active compound is usually from about 25 percent to about 90 percent by weight. The inert carrier is usually chosen from among the attapulgite clays, the montmorillonite clays, the diatomaceous earths, or the purified silicates. Effective surfactants, comprising from about 0.5 percent to about 10 percent by weight of the wettable powder, are chosen from among the sulfonated lignins, the condensed napthalenesulfonates, and the aklyl sulfates.

A typical emulsifiable concentrate comprises from about 0.1 to about 6 pounds of a compound of the invention per gallon of liquid, dissolved in a mixture of organic solvents and emulsifiers. The organic solvent is chosen with regard to its solvency and its cost. Useful solvents include the aromatics, especially the xylenes and the heavy aromatic naphthas. Hydrophilic cosolvents such as cyclohexanone and the glycol ethers such as 2-methoxyethanol may be included. Other organic solvents may also be used, including the terpenic solvents and kerosene. Suitable emulsifiers for emulsifiable concentrates are chosen from the alkylbenzenesulfonates, napthalenesulfonates, and nonionic surfactants such as alkylphenol adducts of polyoxyethylene, and are used at similar percentages as for wettable powders.

Solid, granular compositions are convenient for the application of compounds of this invention to the soil and will contain the active agent in an amount from about 0.1 to about 20% by weight. Granules comprise a compound of the invention dispersed on a granular inert carrier such as coarsely ground clay of from about 0.1 to about 3 mm. particle size. The compound is most conveniently applied to the clay by dissolving it in an inexpensive solvent and applying the solution to the sized clay in an appropriate solids mixer.

The formulated compounds are applied to plants in the manners conventional in agricultural chemistry. Sprayable compositions are easily applied by any of many types of sprayers available to the art. Self-propelled, tractor-mounted, and towed spray devices which apply the water-dispersed formulations through calibrated atomizing nozzles are available and effective. Metering applicators are also available which can apply accurately measured quantities of granular compositions to the soil. The operator of the application equipment need only take care to adjust the equipment to apply an amount of the water-dispersed or granular formulation per acre which supplies the desired application rate of the compound, and to apply the amount uniformly to the plants to be treated.

The following examples provide an illustration of typical herbicidal compositions comprehended by this invention.

| Wettable Powders | |
|---|---|
| Ingredient | Concentration by Weight (Percent) |
| 1-(2,6-Dimethoxybenzoyl)-3-(2,4,6-trifluorophenyl)urea | 50.0 |
| Igepal, a nonionic wetting agent, GAF Corporation | 5.0 |
| Polyfon O, lignosulfonate dispersant, Westvaco Corporation | 5.0 |
| Zeolex 7, a precipitated hydrated silica bulking agent, J. M. Huber Corporation | 5.0 |
| Bardens Clay | 35.0 |
| | 100.0 |

The ingredients are combined and finely ground to provide a free-flowing powder that can be suspended in water for convenient spray application.

| Aqueous Suspension | |
|---|---|
| Ingredient | Concentration by Weight (Percent) |
| 1-(2,6-Dimethoxybenzoyl)-3-(2,6-dichlorophenyl)urea | 45.00 |
| Polyfon H, an anionic lignosulfonate wetting agent and dispersant, | 5.00 |

-continued

Aqueous Suspension

| Ingredient | Concentration by Weight (Percent) |
|---|---|
| Westvaco Corporation | |
| Min-u-gel 200, a clay-type gelling agent, The Floridian Company | 2.00 |
| Antifoam C foam suppressant, Dow Corning Corporation | 0.05 |
| Water | 47.95 |
| | 100.00 |

The above ingredients are intimately admixed and finely ground to provide a suitable suspension, which is then further diluted with water at the application site.

Dust

| Ingredient | Concentration by Weight (Percent) |
|---|---|
| 1-(2,6-Dimethoxybenzoyl)-3-(2,3,5,6-tetrafluorophenyl)urea | 5.0 |
| Diatomite, a diatomaceous earth, Witco Chemical Corporation, Inorganic Specialties Division | 95.0 |
| | 100.0 |

The benzoylphenylurea and diatomaceous earth are intimately mixed and ground to a fine powder of uniform particle size of about 16 to about 40 microns. The dust thus formed may be applied by any number of conventional methods, for example by an aerial application.

Granules

| Ingredient | Concentration by Weight (Percent) |
|---|---|
| 1-(2,6-Dimethoxybenzoyl)-3-(2,3,4,5,6-pentafluorophenyl)urea | 5.0 |
| Heavy aromatic naphtha | 5.0 |
| Florex 30/60 granular clay, The Floridian Company | 90.0 |
| | 100.0 |

The herbicide is dissolved in the naphtha and sprayed onto the clay granules, typically under agitation, and the formulated granules are sieved to provide a uniform mesh size.

The herbicidal activity of representative compounds of the present invention is illustrated by the following experiments.

EXPERIMENT 1

The compounds provided by this invention display herbicidal activity. The initial herbicide test was run at a test compound concentration of 15 lbs./acre (16.8 kg./ha.). In this test a standard sand:soil mixture (1:1) was sterilized at approximately 245° F. for 24 hours in an autoclave. Following sterilization the standard soil mixture was added to separate containers and tomato, large crabgrass and pigweed seeds were planted by row. Each container was then fertilized with a 23-21-17 fertilizer four days before treatment.

The test compounds were formulated for application by dissolving 20 mg. of the compound into 2 ml. of solvent. The solvent was prepared by placing 1.174 g. of Toximul R and 0.783 g. of Toximul S (proprietary blends of anionic and nonionic surfactants manufactured by Stepan Chemical Company, Northfield, Ill.) into 100 ml. of acetone and 100 ml. of ethyl alcohol. The solvent/compound solution was diluted to 8 ml. with deionized water. The solution was applied postemergence to some planted containers and preemergence to others using a modified DeVilbiss atomizer. Postemergence treatment was made 11 to 13 days after planting while preemergence treatment was made one day after planting.

Following treatment the containers were moved to the greenhouse and watered as necessary. Observations were made 10 to 13 days after treatment using untreated control plants as standards. The degree of herbicidal activity was determined by rating the treated plants on a scale of 1 to 5. On this scale "1" indicates no injury, "2" is slight injury, "3" is moderate injury, "4" is severe injury and "5" indicates death to the plant or no seedling emergence. Also, the various types of injury of each test species were coded as follows.

A=abscission of leaves
B=burned
C=chlorosis
D=death
E=epinasty
F=formation effects
G=dark green
I=increased plant growth
L=local necrosis
N=no germination
P=purple pigmentation
R=reduced germination
S=stunting
U=unclassified injury Table I presents the herbicidal activity of typical 2,6-dialkoxybenzoylphenylureas of the present invention when evaluated in the herbicide test described above.

TABLE I

| | Herbicide Pretest at 15 lbs./acre (16.8 kg./ha.) | | | | | |
|---|---|---|---|---|---|---|
| | Preemergence | | | Postemergence | | |
| Example No. of Compound Tested | Tomato | Large Crabgrass | Pigweed | Tomato | Large Crabgrass | Pigweed |
| 1 | 2RS | 1 | 2RS | 1 | 1 | 1 |
| 2 | 5N | 4RS | 5N | 5D | 1 | 5D |
| 3 | 1 | 1 | 1 | 1 | 1 | 1 |
| 4 | 5N | 1 | 5N | 2S | 1 | 1 |
| 5 | 1 | 1 | 1 | 1 | 1 | 1 |
| 8 | 5N | 2S | 5N | 2S | 1 | 1 |

EXPERIMENT 2

The herbicidal activity of some of the compounds of the present invention was further evaluated at various application rates in a multiple species greenhouse test. Several additional weed and crop species were utilized to determine the herbicidal activity and selectivity of the test compounds. The compounds were formulated according to the procedure as described above, except that about 4 g./100 ml. of the compound was dissolved in the surfactant containing solvent and about one part of the organic solution was diluted with 12 parts of water before application to the seed containers. Table II represents preemergence herbicidal test results administered at 8 lbs./acre (8.96 kg./ha.) or less, while Table III represents postemergence test data administered only at 8 lbs./acre.

TABLE II

Preemergence

| Example No. of Compound Tested | Rate of Appln. lbs./acre (kg./ha.) | | Crops | | | | | | | | |
|---|---|---|---|---|---|---|---|---|---|---|---|
| | | | Corn | Cotton | Soybean | Wheat | Alfalfa | Sugar Beet | Rice | Cucumber | Tomato |
| 1 | 8.0 | (8.96) | 1 | | | | | | | | |
| | 4.0 | (4.48) | 1 | 2 | 1 | 1 | | 5 | 1 | 1 | 1 |
| | 2.0 | (2.24) | 1 | 1 | 1 | 1 | | 4 | 1 | 1 | 3 |
| | 1.0 | (1.12) | 1 | 1 | 1 | 1 | | 4 | 1 | 2 | 2 |
| | 1.0 | (1.12) | 1 | 1 | | 1 | 1 | 4 | 3 | 1 | 3 |
| | 0.5 | (0.56) | 1 | 1 | | 1 | 1 | 3 | 1 | 1 | 3 |
| | 0.25 | (0.28) | 1 | 1 | | 1 | 1 | 3 | 1 | 1 | 1 |
| 2 | 8.0 | (8.96) | 2 | | | | | | | | |
| | 4.0 | (4.48) | 3 | 1 | 1 | 1 | 1 | 5 | 1 | 3 | 3 |
| | 2.0 | (2.24) | 1 | 1 | 1 | 1 | 1 | 5 | 1 | 3 | 3 |
| | 1.0 | (1.12) | 1 | 1 | 1 | 1 | 1 | 5 | 1 | 1 | 3 |
| | 1.0 | (1.12) | 1 | 1 | 1 | 1 | 1 | 5 | 1 | 3 | 4 |
| | 0.5 | (0.56) | 1 | 1 | 1 | 1 | 1 | 5 | 1 | 1 | 4 |
| | 0.25 | (0.28) | 1 | 1 | 1 | 1 | 1 | 4 | 1 | 1 | 1 |
| | 0.25 | (0.28) | 1 | 2 | 1 | 1 | 1 | 4 | 1 | 1 | 3 |
| | 0.125 | (0.14) | 1 | 1 | 1 | 1 | 1 | 3 | 1 | 1 | 1 |
| | 0.05 | (0.056) | 1 | 1 | 1 | 1 | 1 | 1 | 1 | 1 | 1 |
| 3 | 8.0 | (8.96) | 1 | | | | | | | | |
| 4 | 8.0 | (8.96) | 3 | | | | | | | | |
| | 4.0 | (4.48) | 1 | 1 | 1 | 1 | 5 | 5 | 1 | 1 | 4 |
| | 2.0 | (2.24) | 2 | 1 | 1 | 1 | 1 | 4 | 1 | 1 | 3 |
| | 1.0 | (1.12) | 1 | 1 | 1 | 1 | 1 | 4 | 1 | 1 | 3 |
| | 1.0 | (1.12) | 1 | 1 | 1 | 1 | 2 | 4 | 1 | 2 | 3 |
| | 0.5 | (0.56) | 1 | 1 | 1 | 1 | 2 | 3 | 1 | 1 | 1 |
| | 0.25 | (0.28) | 1 | 1 | 1 | 1 | 1 | 4 | 1 | 1 | 1 |
| 5 | 8.0 | (8.96) | 2 | | | | | | | | |
| 6 | 8.0 | (8.96) | 4 | | | | | | | | |
| | 4.0 | (4.48) | 2 | 5 | 1 | 1 | 1 | 5 | 2 | 3 | 5 |
| | 2.0 | (2.24) | 1 | 1 | 1 | 1 | 1 | 5 | 1 | 1 | 5 |
| | 1.0 | (1.12) | 1 | 1 | 1 | 1 | 1 | 5 | 1 | 1 | 3 |
| | 1.0 | (1.12) | 2 | 1 | 2 | 1 | 1 | 5 | 2 | 2 | 5 |
| | 0.5 | (0.56) | 1 | 1 | 2 | 1 | 1 | 5 | 2 | 2 | 5 |
| | 0.25 | (0.28) | 1 | 2 | 2 | 1 | 1 | 5 | 1 | 1 | 4 |
| | 0.25 | (0.28) | 1 | 1 | 1 | 1 | 1 | 5 | 1 | 1 | 3 |
| | 0.25 | (0.28) | 1 | 1 | 1 | 1 | 4 | 4 | 1 | 2 | 3 |
| | 0.05 | (0.056) | 1 | 1 | 1 | 1 | 1 | 1 | 1 | 1 | 1 |
| 6 | 0.05 | (0.056) | 1 | 1 | 3 | 1 | 1 | 4 | 2 | 3 | 2 |
| | 0.05 | (0.056) | 1 | 1 | 1 | 1 | 1 | 1 | 1 | 1 | 1 |
| | 0.05 | (0.056) | 1 | 1 | 1 | 1 | 1 | 1 | 1 | 1 | 1 |
| | 0.05 | (0.056) | 1 | 1 | 1 | 1 | 1 | 3 | 1 | 1 | 1 |
| 7 | 8.0 | (8.96) | | | | | | | | | 1 |
| 8 | 8.0 | (8.96) | | | | | | | | | 5 |
| | 4.0 | (4.48) | 1 | 1 | 1 | 1 | 1 | 4 | 1 | 1 | 2 |
| | 2.0 | (2.24) | 2 | 1 | 1 | 1 | 1 | 3 | 1 | 2 | 1 |
| | 1.0 | (1.12) | 1 | 1 | 1 | 1 | 1 | 1 | 1 | 1 | 1 |
| | 1.0 | (1.12) | 1 | 1 | 1 | 1 | 1 | 5 | 2 | 2 | 4 |
| | 0.5 | (0.56) | 1 | 1 | 1 | 1 | 1 | 3 | 1 | 1 | 2 |
| | 0.25 | (0.28) | 1 | 1 | 1 | 1 | 1 | 5 | 1 | 1 | 3 |
| | 0.25 | (0.28) | 2 | 1 | 3 | 2 | 1 | 1 | 2 | 1 | 1 |
| | 0.125 | (0.14) | 1 | 1 | 3 | 2 | 1 | 2 | 1 | 1 | 1 |
| | 0.05 | (0.056) | 1 | 1 | 1 | 1 | 1 | 1 | 1 | 1 | 1 |

| Example No. of Compound Tested | Rate of Appln. lbs./acre (kg./ha.) | | Weeds | | | | | | | | | |
|---|---|---|---|---|---|---|---|---|---|---|---|---|
| | | | Barnyard Grass | Lambsquarter | Large Crabgrass | Mustard | Pigweed | Foxtail | Wild Oat | Velvetleaf | Jimsonweed | Morningglory | Zinnia |
| 1 | 8.0 | (8.96) | | | 1 | | 5 | 1 | | 1 | | 3 | 3 |
| | 4.0 | (4.48) | 1 | 5 | 1 | 2 | 5 | 1 | 1 | 1 | 4 | 2 | 3 |
| | 2.0 | (2.24) | 1 | 5 | 1 | 1 | 5 | 1 | 1 | 1 | 3 | 1 | 2 |
| | 1.0 | (1.12) | 1 | 5 | 1 | 1 | 5 | 1 | 1 | 1 | 3 | 1 | 3 |
| | 1.0 | (1.12) | 1 | 4 | 1 | 1 | 3 | 1 | 1 | 1 | | 1 | 1 |
| | 0.5 | (0.56) | 1 | 3 | 1 | 1 | 3 | 1 | 1 | 1 | | 1 | 2 |
| | 0.25 | (0.28) | 1 | 4 | 1 | 1 | 3 | 1 | 1 | 1 | | 1 | 1 |
| 2 | 8.0 | (8.96) | | | 4 | | 5 | 1 | | 1 | | 4 | 5 |
| | 4.0 | (4.48) | 2 | 5 | 2 | 2 | 5 | 1 | 1 | 1 | 5 | 4 | 5 |
| | 2.0 | (2.24) | 1 | 5 | 2 | 1 | 5 | 1 | 1 | 1 | 5 | 3 | 5 |
| | 1.0 | (1.12) | 1 | 5 | 1 | 1 | 5 | 1 | 1 | 1 | 5 | 4 | 5 |
| | 1.0 | (1.12) | 1 | 5 | 1 | 2 | 5 | 1 | 1 | 1 | | 1 | 4 |
| | 0.5 | (0.56) | 1 | 5 | 1 | 1 | 5 | 1 | 1 | 1 | | 3 | 4 |
| | 0.25 | (0.28) | 1 | 5 | 1 | 1 | 4 | 1 | 1 | 1 | | 1 | 3 |
| | 0.25 | (0.28) | 1 | 5 | 2 | 2 | 5 | 2 | 1 | 1 | | 2 | 3 |
| | 0.125 | (0.14) | 1 | 5 | 2 | 2 | 4 | 2 | 1 | 2 | | 1 | 3 |
| | 0.05 | (0.056) | 1 | 3 | 2 | 2 | 3 | 2 | 1 | 2 | | 1 | 1 |
| 3 | 8.0 | (8.96) | | | 1 | | 1 | 1 | | 1 | | 1 | 2 |
| 4 | 8.0 | (8.96) | | | 4 | | 5 | 3 | | 3 | | 3 | 5 |
| | 4.0 | (4.48) | 3 | 5 | 1 | 4 | 5 | 1 | 3 | 3 | 5 | 1 | 5 |

TABLE II-continued

Preemergence

|   | 2.0 | (2.24) | 1 | 5 | 1 | 4 | 5 | 1 | 2 | 1 | 3 | 2 | 5 |
|---|---|---|---|---|---|---|---|---|---|---|---|---|---|
|   | 1.0 | (1.12) | 1 | 5 | 1 | 5 | 5 | 1 | 1 | 1 | 4 | 1 | 4 |
|   | 1.0 | (1.12) | 1 | 5 | 1 | 1 | 4 | 1 | 1 | 1 |   | 2 | 5 |
|   | 0.5 | (0.56) | 1 | 5 | 1 | 2 | 3 | 1 | 1 | 1 |   | 1 | 3 |
|   | 0.25 | (0.28) | 1 | 5 | 1 | 2 | 3 | 1 | 1 | 1 |   | 1 | 3 |
| 5 | 8.0 | (8.96) |   |   | 4 |   | 3 | 2 |   | 2 |   | 2 | 2 |
| 6 | 8.0 | (8.96) |   |   | 5 |   | 5 | 3 |   | 2 |   | 4 | 3 |
|   | 4.0 | (4.48) | 5 | 5 | 2 | 2 | 5 | 2 | 1 | 2 | 5 | 4 | 5 |
|   | 2.0 | (2.24) | 4 | 5 | 2 | 2 | 5 | 3 | 2 | 1 | 5 | 5 | 5 |
|   | 1.0 | (1.12) | 2 | 5 | 2 | 4 | 5 | 2 | 1 | 1 | 5 | 2 | 5 |
|   | 1.0 | (1.12) | 3 | 5 | 3 | 3 | 5 | 1 | 1 | 2 | 5 | 2 | 5 |
|   | 0.5 | (0.56) | 2 | 5 | 2 | 2 | 5 | 1 | 1 | 2 | 1 | 2 | 5 |
|   | 0.25 | (0.28) | 1 | 5 | 2 | 2 | 5 | 1 | 1 | 2 | 1 | 2 | 4 |
|   | 0.25 | (0.28) | 1 | 5 | 1 | 2 | 4 | 1 | 1 | 1 | 3 | 1 | 2 |
|   | 0.25 | (0.28) | 1 | 5 | 2 | 2 | 5 | 1 | 1 | 1 | 4 | 3 | 3 |
| 6 | 0.05 | (0.056) | 1 | 3 | 1 | 1 | 3 | 1 | 1 | 1 | 2 | 1 | 1 |
|   | 0.05 | (0.056) |   | 5 | 1 | 1 | 1 | 2 | 1 | 2 |   |   |   |
|   | 0.05 | (0.056) | 1 | 1 | 1 | 1 | 1 | 1 | 1 | 1 | 1 | 1 | 1 |
|   | 0.05 | (0.056) | 1 | 4 | 1 | 1 | 1 | 1 | 1 | 1 | 1 | 1 | 1 |
|   | 0.05 | (0.056) | 1 | 3 | 1 | 1 | 2 | 1 | 1 | 1 | 1 | 1 | 1 |
| 7 | 8.0 | (8.96) | 1 |   | 1 | 1 | 4 | 1 | 1 | 2 |   | 1 | 1 |
| 8 | 8.0 | (8.96) | 1 |   | 2 | 2 | 5 | 2 | 1 | 1 |   | 2 | 5 |
|   | 4.0 | (4.48) | 4 | 5 | 2 | 2 | 4 | 3 | 1 | 2 | 4 | 1 | 3 |
|   | 2.0 | (2.24) | 2 | 5 | 1 | 3 | 4 | 2 | 1 | 2 | 2 | 1 | 4 |
|   | 1.0 | (1.12) | 1 | 4 | 1 | 1 | 4 | 1 | 1 | 2 | 2 | 1 | 5 |
|   | 1.0 | (1.12) | 2 | 5 | 1 | 4 | 5 | 1 | 1 | 1 | 2 | 1 | 4 |
|   | 0.5 | (0.56) | 3 | 5 | 2 | 2 | 3 | 1 | 1 | 1 | 3 | 1 | 2 |
|   | 0.25 | (0.28) | 3 | 5 | 1 | 1 | 4 | 1 | 1 | 2 | 2 | 1 | 2 |
|   | 0.25 | (0.28) | 1 | 5 | 2 | 1 | 3 | 2 | 1 | 2 | 1 | 2 | 1 |
|   | 0.125 | (0.14) | 1 | 3 | 2 | 1 | 2 | 1 | 1 | 1 | 1 | 1 | 1 |
|   | 0.05 | (0.056) | 1 | 1 | 2 | 1 | 1 | 1 | 1 | 1 | 1 | 1 | 1 |

TABLE III

Postemergence

| Example No. of Compound Tested | Rate of Appln. lbs./acre (kg./ha.) | Corn | Tomato | Large Crabgrass | Pigweed | Foxtail | Velvetleaf | Morningglory | Zinnia | Barnyard Grass | Mustard | Wildoat |
|---|---|---|---|---|---|---|---|---|---|---|---|---|
| 1 | 8.0 (8.96) | 1 |   | 1 | 2 | 1 | 1 | 1 | 1 |   |   |   |
| 2 | 8.0 (8.96) | 1 |   | 1 | 3 | 1 | 2 | 3 | 2 |   |   |   |
| 3 | 8.0 (8.96) | 1 |   | 1 | 1 | 1 | 1 | 1 | 1 |   |   |   |
| 4 | 8.0 (8.96) | 1 |   | 1 | 2 | 1 | 2 | 2 | 2 |   |   |   |
| 5 | 8.0 (8.96) | 1 |   | 1 | 1 | 1 | 1 | 1 | 1 |   |   |   |
| 6 | 8.0 (8.96) | 1 |   | 1 | 3 | 2 | 2 | 2 | 3 |   |   |   |
| 7 | 8.0 (8.96) |   | 1 | 1 | 2 | 3 | 1 | 1 | 1 | 1 | 1 | 1 |
| 8 | 8.0 (8.96) |   | 2 | 1 | 2 | 1 | 1 | 1 | 1 | 1 | 2 | 1 |

EXPERIMENT 3

Example 2 of the present invention, 1-(2,6-dimethoxybenzoyl)-3-(2,6-difluorophenyl)urea, was also tested in a field study to evaluate the compound's herbicidal activity and crop tolerance.

The compound was formulated as a 50 % wettable powder according to the following procedure. 127.2 g. of Example 2 was intimately mixed with 19.8 g. Reax 45L (a surfactant plus lignosulfonate, which acts as a combination wetting and dispersing agent, made by Westvaco), 12.3 g. Zeolex 7 (a precipitated silica made by J. M. Huber Corp.), and 87.7 g. Barden's Clay (a kaolinite clay made by J. M. Huber Corp.). This mixture was then milled to the required particle size through a hammer mill or a fluid energy mill.

The formulated compound diluted with water was both surface applied and pre-plant incorporated at various application rates to assorted crop and weed species. Crop injury ratings were made visually on a scale of 0-10, with 0 being no injury and 10 being plant death, and this number was multiplied by 10 to obtain a percent inhibition. Three replications were done at each rate and the average percent inhibition entered in the table. Observations were made at 3 and 6 weeks after planting (and treatment). The results of the field test are reported below in Table IV (surface applied) and Table V (pre-plant incorporated). A dash (-) in the tables indicate that the compound was not tested at that specific concentration against the indicated plant species.

TABLE IV

Surface Applied

| Appln. rate lbs./acre (kg./ha.) | Weeks after planting | Crops | | | | | | | Weeds | | | | |
| | | Sorghum | Field corn | Rice | Barley | Wheat | Soybean | Cotton | Annual Grasses | Velvetleaf | Redroot Pigweed | Morningglory | Mustard |
|---|---|---|---|---|---|---|---|---|---|---|---|---|---|
| 4.0 (4.48) | 3 | 3.3 | 0 | 3.3 | — | — | 0 | 0 | 12.2 | 26.7 | 100 | 26.7 | — |
|  | 6 | 0 | 0 | — | — | — | 0 | 0 | 13.3 | — | 100 | 15.0 | — |

TABLE IV-continued

Surface Applied

| Appln. rate lbs./acre (kg./ha.) | | Weeks after planting | Crops | | | | | | | Weeds | | | | |
|---|---|---|---|---|---|---|---|---|---|---|---|---|---|---|
| | | | Sorghum | Field corn | Rice | Bar-ley | Wheat | Soy-bean | Cotton | Annual Grasses | Velvet-leaf | Redroot Pigweed | Morning-glory | Mustard |
| 3.0 | (3.36) | 3 | — | — | 3.3 | 0 | 0 | — | — | 30.0 | — | — | — | 74.0 |
| | | 6 | — | — | — | 0 | 0 | — | — | 0 | — | — | — | 70.0 |
| 2.0 | (2.24) | 3 | 0 | 0 | 0 | — | — | 0 | 0 | 5.6 | 15 | 100 | 8.4 | — |
| | | 6 | 0 | 0 | — | — | — | 0 | .0 | 9.4 | — | 83.3 | 7.5 | — |
| 1.5 | (1.60) | 3 | — | — | — | 10.0 | 5.0 | — | — | 25.0 | — | — | — | 20.0 |
| | | 6 | — | — | — | 0 | 0 | — | — | — | — | — | — | 30.0 |
| 1.0 | (1.12) | 3 | 0 | 0 | 0 | — | — | 0 | 0 | 4.4 | 13.3 | 100 | 28.4 | — |
| | | 6 | 0 | 0 | — | — | — | 0 | 0 | 0 | — | 100 | 10.8 | — |
| 0.75 | (0.84) | 3 | — | — | — | 0 | 0 | — | — | 0 | — | — | — | 0 |
| | | 6 | — | — | — | 0 | 0 | — | — | — | — | — | — | 30.0 |
| 0.5 | (0.56) | 3 | 0 | 0 | — | — | — | 0 | 0 | 0 | 13.3 | 96.7 | 11.6 | — |
| | | 6 | 0 | 0 | — | — | — | 0 | 0 | 0 | — | 96.0 | 0 | — |
| 0.375 | (0.42) | 3 | — | — | — | 0 | 0 | — | — | 0 | — | — | — | 0 |
| | | 6 | — | — | — | 0 | 0 | — | — | — | — | — | — | 0 |

TABLE V

Pre-Plant Incorporated

| Appln. rate lbs./acre (kg./ha.) | | Weeks after planting | Crops | | | | | | Weeds | | | | |
|---|---|---|---|---|---|---|---|---|---|---|---|---|---|
| | | | Sorghum | Field corn | Barley | Wheat | Soybean | Cotton | Annual Grasses | Velvet-leaf | Redroot Pigweed | Morning-glory | Mustard |
| 3.0 | (3.36) | 3 | 10.0 | 6.7 | — | — | 20.0 | 3.3 | 36.7 | 13.3 | 100 | 65.0 | — |
| | | 6 | 0 | 0 | — | — | 3.3 | 0 | 11.7 | — | 100 | 74.7 | — |
| 2.0 | (2.24) | 3 | — | — | 0 | 0 | — | — | 25.0 | — | — | — | 15.0 |
| | | 6 | — | — | 0 | 0 | — | — | — | — | — | — | 0 |
| 1.5 | (1.68) | 3 | 6.7 | 0 | — | — | 0 | 0 | 11.7 | 6.7 | 100 | 38.3 | — |
| | | 6 | 0 | 0 | — | — | 0 | 0 | 10.8 | — | 100 | 43.3 | — |
| 1.0 | (1.12) | 3 | — | — | 15.0 | 0 | — | — | 15.0 | — | — | — | 0 |
| | | 6 | — | — | 0 | 0 | — | — | — | — | — | — | 0 |
| 0.75 | (0.84) | 3 | 10.0 | 10.0 | — | — | 0 | 0 | 13.3 | 0 | 96.7 | 16.7 | — |
| | | 6 | 0 | 0 | — | — | 0 | 6.7 | 0 | — | 86.7 | 0 | — |
| 0.50 | (0.56) | 3 | — | — | 0 | 0 | — | — | 0 | — | — | — | 0 |
| | | 6 | — | — | 0 | 0 | — | — | — | — | — | — | 25.0 |
| 0.375 | (0.42) | 3 | 0 | 0 | — | — | 0 | 0 | 0 | 6.7 | 76.7 | 6.7 | — |
| | | 6 | 0 | 0 | — | — | 0 | 0 | 0 | — | 68.3 | 6.7 | — |
| 0.25 | (0.28) | 3 | — | — | 0 | 0 | — | — | 0 | — | — | — | 0 |
| | | 6 | — | — | 0 | 0 | — | — | — | — | — | — | 25.0 |

EXPERIMENT 4

A field study was also conducted in Great Britain to determine the efficacy and selectivity of Example 2 of the present invention against a variety of crop and weed species. The compound was formulated employing Toximul R and S as surfactants and a 1:1 mixture of acetone:ethanol by the general procedure outlined above. The formulated compound was then surface applied preemergence to the soil surface. Observations were made to determine the compound's effect against crop species barley and wheat by comparing the crop's emergence to untreated control plots, as well as the compound's ability to control certain weed species. Control ratings are given in percentage of control compared to untreated control plots based upon visual inspection. These results appear in Table VI below.

TABLE VI

| Observation | Days After Treatment | Rate kg./ha. | Percent |
|---|---|---|---|
| Percent of Barley Plants Emerged | 14 | 1.0 | 94.0 |
| | | 0.5 | 97.0 |
| | | 0.25 | 91.2 |
| | | 0.125 | 87.8 |
| | | Untreated Control | 100.0 |
| Percent Crop Injury of Barley Plants Emerged | 28 | 1.0 | 0.8 |
| | | 0.5 | 2.3 |
| | | 0.25 | 0 |

TABLE VI-continued

| Observation | Days After Treatment | Rate kg./ha. | Percent |
|---|---|---|---|
| | | 0.125 | 1.6 |
| | | Untreated Control | 0 |
| Percent Crop Vigor of Barley Plants Emerged | 28 | 1.0 | 97.9 |
| | | 0.5 | 92.0 |
| | | 0.25 | 97.9 |
| | | 0.125 | 97.9 |
| | | Untreated Control | 100.0 |
| | 37 | 1.0 | 104.8 |
| | | 0.5 | 108.5 |
| | | 0.25 | 111.5 |
| | | 0.125 | 108.5 |
| | | Untreated Control | 100.0 |
| Percent of Common Wheat Plants Emerged | 14 | 1.0 | 92.4 |
| | | 0.5 | 103.2 |
| | | 0.25 | 103.4 |
| | | 0.125 | 85.5 |
| | | Untreated Control | 100.0 |
| Percent Crop Injury of Common Wheat Plants Emerged | 28 | 1.0 | 1.3 |
| | | 0.5 | 1.0 |
| | | 0.25 | 0.7 |
| | | 0.125 | 1.3 |
| | | Untreated Control | 0.7 |
| Percent Crop Vigor of Common Wheat Plants Emerged | 28 | 1.0 | 96.1 |
| | | 0.5 | 91.6 |
| | | 0.25 | 91.6 |
| | | 0.125 | 91.6 |
| | | Untreated Control | 100.0 |
| | 39 | 1.0 | 100.0 |
| | | 0.5 | 79.6 |
| | | 0.25 | 70.9 |

TABLE VI-continued

| Observation | Days After Treatment | Rate kg./ha. | Percent |
|---|---|---|---|
| | | 0.125 | 79.6 |
| | | Untreated Control | 100.0 |
| Control of Blackgrass | 28 | 1.0 | 2.3 |
| | | 0.5 | 0 |
| | | 0.25 | 4.7 |
| | | 0.125 | 0 |
| | | Untreated Control | 0 |
| | 42 | 1.0 | 4.7 |
| | | 0.5 | 0 |
| | | 0.25 | 1.6 |
| | | 0.125 | 0 |
| | | Untreated Control | 0 |
| Control of Catchweed Bedstraw | 28 | 1.0 | 7.4 |
| | | 0.5 | 0 |
| | | 0.25 | 0 |
| | | 0.125 | 2.9 |
| | | Untreated Control | 0 |
| | 42 | 1.0 | 14.9 |
| | | 0.5 | 0 |
| | | 0.25 | 2.3 |
| | | 0.125 | 4.7 |
| | | Untreated Control | 0 |
| Control of Wild Chamomile | 28 | 1.0 | 100.0 |
| | | 0.5 | 98.4 |
| | | 0.25 | 96.3 |
| | | 0.125 | 52.8 |
| | | Untreated Control | 0 |
| | 42 | 1.0 | 100.0 |
| | | 0.5 | 99.2 |
| | | 0.25 | 97.0 |
| | | 0.125 | 76.4 |
| | | Untreated Control | 0 |
| Control of Common Chickweed | 28 | 1.0 | 100.0 |
| | | 0.5 | 100.0 |
| | | 0.25 | 100.0 |
| | | 0.125 | 98.4 |
| | | Untreated Control | 0 |
| | 42 | 1.0 | 100.0 |
| | | 0.5 | 100.0 |
| | | 0.25 | 99.2 |
| | | 0.125 | 70.2 |
| | | Untreated Control | 0 |
| Control of Birdseye Speedwell | 42 | 1.0 | 100.0 |
| | | 0.5 | 100.0 |
| | | 0.25 | 85.1 |
| | | 0.125 | 100.0 |
| | | Untreated Control | 0 |

As noted above, the compounds of the present invention may also be used in combination with one or more herbicides. Such combinations are preferred when a broader spectrum of weed control is desired than either herbicide can provide when used alone. For example, the present compounds may be combined with one or more grass herbicides. Preferred grass herbicides to be employed in these combinations include the dinitroanilines, such as trifluralin, benefin, butralin, chlornidine, dinitramine, ethalfluralin, fluchloralin, isopropalin, nitralin, oryzalin, pendimethalin, prodiamine, profluralin, prosulfalin, and the like. The most preferred combination of the present invention is comprised of trifluralin and 1-(2,6-dimethoxybenzoyl)-3-(2,6-difluorophenyl)urea. Other herbicides which may be used in combination with a presently disclosed benzoylurea include alachlor, ametryn, amitrole, atrazine, bentazon, bifenox, butachlor, butam, buthidazole, butylate, chloramben, chlorbromuron, cyanazine, dichlorprop, diuron, dinoseb, EPTC, fenac, fluometuron, linuron, methazole, metolachlor, metribuzin, nitrofen, norflurazon, pebulate, perfluidone, prometon, prometryn, propachlor, simazine, tebuthiuron, terbutryn, triallate, triclopyr, propanil, vernolate and the like.

Also provided by this invention is a method for controlling undesired plants which comprises applying to the plants a growth inhibiting amount of a combination of a present benzoylphenylurea together with another herbicide. The application rate desired for each of the individual herbicides in the combination is dependent on a number of factors, including the type of weeds and grasses to be controlled, the herbicides that will be used in the combination, climate and soil conditions, the weed population and related factors. Generally, the present compounds will be employed in combination with other herbicides in a ratio of about one to about ten parts by weight of benzoylphenylurea and about ten to about one part by weight of another herbicide. More preferable ratios of active ingredients will be from about one to about five parts by weight of a present compound and about five to about one part by weight of another herbicide. A particularly preferred combination will contain the component herbicides in a weight ratio of about one to one. The combinations will be applied at rates which are effective to control the undesired plants to the desired degree.

The combinations provided herein are formulated in the identical manner which was described for the present novel compounds alone, and at similar concentrations. The active components of the combination may be combined as technical materials and later formulated as a whole, or formulated individually and applied either as a combination or individually to the locus of the undesired plants.

The following is an example of a typical herbicidal composition containing a combination of the invention.

| Tank-Mix Composition | |
|---|---|
| Ingredient | Concentration by Weight (Percent) |
| 1-(2,6-Dimethoxybenzoyl)-3-(2,6-difluorophenyl)urea formulated as a 50% wettable powder | 60.0 |
| Trifluralin formulated as a 4EC | 40.0 |
| | 100.0 |

The wettable powder formulation containing 50% by weight of the active ingredient is added to water and the mixture agitated while adding the emulsifiable concentrate containing the trifluralin at the rate of 4 lbs./gal. The mixture is sprayed on the soil surface and then typically incorporated at a depth of about 3 to 4 inches prior to planting.

The herbicidal activity of representative combinations of the present invention is illustrated by the following field studies.

EXPERIMENT 5

A field study was performed using a combination of Example 2 of the present invention and trifluralin as the active ingredient. The compounds were tank-mix formulated for use in this experiment by adding Example 2 as a 50% wettable powder to water under agitation and then combining to this mixture an emulsifiable concentrate containing trifluralin at a concentration of 4 lbs./gallon. The combination was then preplant incorporated at a depth of three inches into the soil and seeded the same day with soybeans and cotton. The data is recorded as percent inhibition. The results of this test appear below in Table VII.

TABLE VII

| Example 2 + trifluralin Appln. rate lbs./acre (kg./ha.) | Days after planting | Example 2 and Trifluralin in Combination ||||
|---|---|---|---|---|---|---|
| | | Soybean | Cotton | Jimson weed | Giant Foxtail | Cocklebur |
| 2.0 + 0.5 (2.24 + 0.56) | 20 | 0.3 | 5.0 | 100.0 | 97.5 | 99.5 |
| (2.24 + 0.56) | 35 | 0 | 0 | 100.0 | 97.5 | 98.2 |
| 1.5 + 0.5 (1.68 + 0.56) | 20 | 0 | 0 | 98.8 | 100.0 | 99.7 |
| (1.68 + 0.56) | 35 | 0 | 0 | 97.5 | 98.8 | 98.8 |
| 1.0 + 0.5 (1.12 + 0.56) | 20 | 0 | 0 | 98.2 | 99.0 | 98.0 |
| (1.12 + 0.56) | 35 | 0 | 0 | 94.5 | 95.7 | 94.5 |
| 0.5 + 0.5 (0.56 + 0.56) | 20 | 0 | 0 | 93.8 | 100.0 | 93.5 |
| (0.56 + 0.56) | 35 | 0 | 0 | 73.8 | 99.5 | 87.5 |

EXPERIMENT 6

A field study was also conducted in Mississippi using a combination of Example 2 and trifluralin on cotton against a wide variety of weed species. The combination was tank mix formulated and preplant incorporated as above, and the crop was seeded 5 days post treatment. The results of this test appear below in Table VIII.

TABLE VIII

| Observation | Days After Treatment | Example 2 + trifluralin Application Rate (kg./ha.) lbs./acre | Percent |
|---|---|---|---|
| Injury to Cotton Plants 2-3 inches tall | 40 | 2.0 + 0.75 (2.24 + 0.84) | 0 |
| | | 1.5 + 0.75 (1.68 + 0.84) | 0 |
| | | 1.0 + 0.75 (1.12 + 0.84) | 0 |
| | | 0.75 + 0.75 (0.84 + 0.84) | 0 |
| | | 0.50 + 0.75 (0.56 + 0.84) | 0 |
| | | 0.25 + 0.75 (0.28 + 0.84) | 0 |
| | | Untreated Control | 0 |
| Injury to Cotton Plants at Early Flowering Stage | 90 | 2.0 + 0.75 (2.24 + 0.84) | 0 |
| | | 1.5 + 0.75 (1.68 + 0.84) | 0 |
| | | 1.0 + 0.75 (1.12 + 0.84) | 0 |
| | | 0.75 + 0.75 (0.84 + 0.84) | 0 |
| | | 0.50 + 0.75 (0.56 + 0.84) | 0 |
| | | 0.25 + 0.75 (0.28 + 0.84) | 0 |
| | | Untreated Control | 0 |
| Injury to Cotton Plants having 50 to 60% open bolls | 181 | 2.0 + 0.75 (2.24 + 0.84) | 0 |
| | | 1.5 + 0.75 (1.68 + 0.84) | 0 |
| | | 1.0 + 0.75 (1.12 + 0.84) | 0 |
| | | 0.75 + 0.75 (0.84 + 0.84) | 0 |
| | | 0.50 + 0.75 (0.56 + 0.84) | 0 |
| | | 0.25 + 0.75 (0.28 + 0.84) | 0 |
| | | Untreated Control | 0 |
| No. of Cotton Plants for every two 10 foot rows | 51 | 2.0 + 0.75 (2.24 + 0.84) | 109.7 |
| | | 1.5 + 0.75 (1.68 + 0.84) | 102.6 |
| | | 1.0 + 0.75 (1.12 + 0.84) | 97.4 |
| | | 0.75 + 0.75 (0.84 + 0.84) | 90.3 |
| | | 0.50 + 0.75 (0.56 + 0.84) | 102.6 |
| | | 0.25 + 0.75 (0.28 + 0.84) | 95.4 |
| | | Untreated Control | 100.0 |
| Pounds of Seed Cotton per 317 sq. ft. | 195 | 2.0 + 0.75 (2.24 + 0.84) | 116.7 |
| | | 1.5 + 0.75 (1.68 + 0.84) | 134.4 |
| | | 1.0 + 0.75 (1.12 + 0.84) | 126.7 |
| | | 0.75 + 0.75 (0.84 + 0.84) | 132.2 |
| | | 0.50 + 0.75 (0.56 + 0.84) | 118.9 |
| | | 0.25 + 0.75 (0.28 + 0.84) | 113.3 |
| | | Untreated Control | 100.0 |
| Control of Redroot Pigweed | 40 | 2.0 + 0.75 (2.24 + 0.84) | 100.0 |
| | | 1.5 + 0.75 (1.68 + 0.84) | 100.0 |
| | | 1.0 + 0.75 (1.12 + 0.84) | 100.0 |
| | | 0.75 + 0.75 (0.84 + 0.84) | 100.0 |
| | | 0.50 + 0.75 (0.56 + 0.84) | 100.0 |
| | | 0.25 + 0.75 (0.28 + 0.84) | 100.0 |
| | | Untreated Control | 0 |
| | 90 | 2.0 + 0.75 (2.24 + 0.84) | 100.0 |
| | | 1.5 + 0.75 (1.68 + 0.84) | 100.0 |
| | | 1.0 + 0.75 (1.12 + 0.84) | 100.0 |
| | | 0.75 + 0.75 (0.84 + 0.84) | 100.0 |
| | | 0.50 + 0.75 (0.56 + 0.84) | 100.0 |
| | | 0.25 + 0.75 (0.28 + 0.84) | 100.0 |
| | | Untreated Control | 0 |
| | 181 | 2.0 + 0.75 (2.24 + 0.84) | 100.0 |
| | | 1.5 + 0.75 (1.68 + 0.84) | 100.0 |
| | | 1.0 + 0.75 (1.12 + 0.84) | 100.0 |
| | | 0.75 + 0.75 (0.84 + 0.84) | 100.0 |
| | | 0.50 + 0.75 (0.56 + 0.84) | 100.0 |
| | | 0.25 + 0.75 (0.28 + 0.84) | 100.0 |
| | | Untreated Control | 0 |
| Control of Common Purslane | 40 | 2.0 + 0.75 (2.24 + 0.84) | 100.0 |
| | | 1.5 + 0.75 (1.68 + 0.84) | 100.0 |
| | | 1.0 + 0.75 (1.12 + 0.84) | 100.0 |
| | | 0.75 + 0.75 (0.84 + 0.84) | 100.0 |
| | | 0.50 + 0.75 (0.56 + 0.84) | 98.3 |
| | | 0.25 + 0.75 (0.28 + 0.84) | 100.0 |
| | | Untreated Control | 0 |
| | 90 | 2.0 + 0.75 (2.24 + 0.84) | 100.0 |
| | | 1.5 + 0.75 (1.68 + 0.84) | 100.0 |
| | | 1.0 + 0.75 (1.12 + 0.84) | 100.0 |
| | | 0.75 + 0.75 (0.84 + 0.84) | 100.0 |
| | | 0.50 + 0.75 (0.56 + 0.84) | 100.0 |
| | | 0.25 + 0.75 (0.28 + 0.84) | 93.3 |
| | | Untreated Control | 0 |
| Control of Foxtail Millet | 40 | 2.0 + 0.75 (2.24 + 0.84) | 100.0 |
| | | 1.5 + 0.75 (1.68 + 0.84) | 99.3 |
| | | 1.0 + 0.75 (1.12 + 0.84) | 100.0 |
| | | 0.75 + 0.75 (0.84 + 0.84) | 100.0 |
| | | 0.50 + 0.75 (0.56 + 0.84) | 100.0 |
| | | 0.25 + 0.75 (0.28 + 0.84) | 100.0 |
| | | Untreated Control | 0 |
| Control of Prickly Sida | 40 | 2.0 + 0.75 (2.24 + 0.84) | 33.3 |
| | | 1.5 + 0.75 (1.68 + 0.84) | 6.7 |
| | | 1.0 + 0.75 (1.12 + 0.84) | 0 |
| | | 0.75 + 0.75 (0.84 + 0.84) | 0 |
| | | 0.50 + 0.75 (0.56 + 0.84) | 0 |
| | | 0.25 + 0.75 (0.28 + 0.84) | 0 |
| | | Untreated Control | 0 |
| | 90 | 2.0 + 0.75 (2.24 + 0.84) | 60.0 |
| | | 1.5 + 0.75 (1.68 + 0.84) | 0 |
| | | 1.0 + 0.75 (1.12 + 0.84) | 0 |
| | | 0.75 + 0.75 (0.84 + 0.84) | 0 |
| | | 0.50 + 0.75 (0.56 + 0.84) | 16.7 |
| | | 0.25 + 0.75 (0.28 + 0.84) | 0 |
| | | Untreated Control | 0 |
| | 181 | 2.0 + 0.75 (2.24 + 0.84) | 75.0 |
| | | 1.5 + 0.75 (1.68 + 0.84) | 23.3 |
| | | 1.0 + 0.75 (1.12 + 0.84) | 0 |
| | | 0.75 + 0.75 (0.84 + 0.84) | 10.0 |
| | | 0.50 + 0.75 (0.56 + 0.84) | 13.3 |
| | | 0.25 + 0.75 (0.28 + 0.84) | 0 |
| | | Untreated Control | 0 |
| Control of Cocklebur | 40 | 2.0 + 0.75 (2.24 + 0.84) | 93.3 |
| | | 1.5 + 0.75 (1.68 + 0.84) | 96.7 |
| | | 1.0 + 0.75 (1.12 + 0.84) | 90.0 |
| | | 0.75 + 0.75 (0.84 + 0.84) | 78.3 |
| | | 0.50 + 0.75 (0.56 + 0.84) | 53.3 |
| | | 0.25 + 0.75 (0.28 + 0.84) | 20.0 |
| | | Untreated Control | 0 |
| | 90 | 2.0 + 0.75 (2.24 + 0.84) | 100.0 |
| | | 1.5 + 0.75 (1.68 + 0.84) | 100.0 |
| | | 1.0 + 0.75 (1.12 + 0.84) | 100.0 |
| | | 0.75 + 0.75 (0.84 + 0.84) | 100.0 |
| | | 0.50 + 0.75 (0.56 + 0.84) | 96.7 |
| | | 0.25 + 0.75 (0.28 + 0.84) | 93.7 |
| | | Untreated Control | 0 |

EXPERIMENT 7

A field study was conducted in Brazil to evaluate the herbicidal activity and crop tolerance of Example 2 of the present invention both alone and in combination with either ethalfluralin or oryzalin. Example 2 was formulated for both tests as a 50% wettable powder. When combined with Example 2, oryzalin was formulated as an aqueous suspension containing the active at a rate of 4 lbs./gallon. In this test the formulations were tank mixed and surface applied to the soil surface following planting. Ethalfluralin was formulated as an emulsifiable concentrate containing the active at a rate of 3 lbs./gallon, combined with Example 2 and diluted with water to again provide a tank mix composition. This formulation was then incorporated into the soil following planting with a flexible tooth harrow. Observations were then recorded following visual comparison of treated plots and untreated controls. Table IX which follows presents the results of the combination of Example 2 and ethalfluralin, while Table X provides data for the combination of Example 2 and oryzalin.

TABLE IX

Example 2 and Ethalfluralin in Combination

| Observation | Days After Treatment | Treatment | Rate kg./ha. | Percent |
|---|---|---|---|---|
| Rice Injury | 16 | Example 2 + Ethalfluralin | 1.5 + 0.9 | 0 |
| | | | 1.0 + 0.9 | 0 |
| | | | 0.75 + 0.9 | 0 |
| | | | 0.5 + 0.9 | 1.3 |
| | | Example 2 | 1.0 | 0 |
| | | Untreated Control | | 0 |
| | 37 | Example 2 + Ethalfluralin | 1.5 + 0.9 | 0 |
| | | | 1.0 + 0.9 | 0 |
| | | | 0.75 + 0.9 | 2.5 |
| | | | 0.5 + 0.9 | 2.5 |
| | | Example 2 | 1.0 | 0 |
| | | Untreated Control | | 0 |
| Root Injury to Rice | 16 | Example 2 + Ethalfluralin | 1.5 + 0.9 | 0 |
| | | | 1.0 + 0.9 | 0 |
| | | | 0.75 + 0.9 | 0 |
| | | | 0.5 + 0.9 | 0 |
| | | Example 2 | 1.0 | 0 |
| | | Untreated Control | | 0 |
| | 37 | Example 2 + Ethalfluralin | 1.5 + 0.9 | 0 |
| | | | 1.0 + 0.9 | 2.5 |
| | | | 0.75 + 0.9 | 0 |
| | | | 0.5 + 0.9 | 0 |
| | | Example 2 | 1.0 | 0 |
| | | Untreated Control | | 0 |
| Control of Goosegrass | 37 | Example 2 + Ethalfluralin | 1.5 + 0.9 | 97.5 |
| | | | 1.0 + 0.9 | 97.5 |
| | | | 0.75 + 0.9 | 95.0 |
| | | | 0.5 + 0.9 | 95.0 |
| | | Example 2 | 1.0 | 0 |
| | | Untreated Control | | 0 |
| Control of Morningglory | 37 | Example 2 + Ethalfluralin | 1.5 + 0.9 | 75.0 |
| | | | 1.0 + 0.9 | 82.5 |
| | | | 0.75 + 0.9 | 77.5 |
| | | | 0.5 + 0.9 | 66.3 |
| | | Example 2 | 1.0 | 0 |
| | | Untreated Control | | 0 |
| Control of Common Purslane | 37 | Example 2 + Ethalfluralin | 1.5 + 0.9 | 97.5 |
| | | | 1.0 + 0.9 | 100.0 |
| | | | 0.75 + 0.9 | 100.0 |
| | | | 0.5 + 0.9 | 100.0 |
| | | Example 2 | 1.0 | 100.0 |
| | | Untreated Control | | 0 |
| Control of Brazil Calalilly | 37 | Example 2 + Ethalfluralin | 1.5 + 0.9 | 90.0 |
| | | | 1.0 + 0.9 | 82.5 |
| | | | 0.75 + 0.9 | 82.5 |
| | | | 0.5 + 0.9 | 77.5 |
| | | Example 2 | 1.0 | 0 |
| | | Untreated Control | | 0 |

TABLE X

Example 2 and Oryzalin in Combination

| Observation | Days After Treatment | Treatment | Rate kg./ha. | Percent |
|---|---|---|---|---|
| Soybean Injury | 17 | Example 2 + Oryzalin | 1.5 + 1.5 | 0 |
| | | | 1.0 + 1.5 | 0 |
| | | | 0.75 + 1.5 | 0 |
| | | Example 2 | 1.0 | 0 |
| | | Untreated Control | | 0 |
| | 31 | Example 2 + Oryzalin | 1.5 + 1.5 | 7.5 |
| | | | 1.0 + 1.5 | 0 |
| | | | 0.75 + 1.5 | 0 |
| | | Example 2 | 1.0 | 5.0 |
| | | Untreated Control | | 0 |
| Soybean Emergence | 31 | Example 2 + Oryzalin | 1.5 + 1.5 | 82.7 |
| | | | 1.0 + 1.5 | 75.6 |
| | | | 0.75 + 1.5 | 96.6 |
| | | Example 2 | 1.0 | 82.2 |
| | | Untreated Control | | 100.0 |
| Root Injury to Soybean | 17 | Example 2 + Oryzalin | 1.5 + 1.5 | 0 |
| | | | 1.0 + 1.5 | 0 |
| | | | 0.75 + 1.5 | 0 |
| | | Example 2 | 1.0 | 0 |
| | | Untreated Control | | 0 |
| | 31 | Example 2 + Oryzalin | 1.5 + 1.5 | 10.0 |
| | | | 1.0 + 1.5 | 7.5 |
| | | | 0.75 + 1.5 | 10.0 |
| | | Example 2 | 1.0 | 5.0 |
| | | Untreated Control | | 0 |
| Control of Southern Sanbur | 31 | Example 2 + Oryzalin | 1.5 + 1.5 | 98.2 |
| | | | 1.0 + 1.5 | 95.0 |
| | | | 0.75 + 1.5 | 96.3 |
| | | Example 2 | 1.0 | 0 |
| | | Untreated Control | | 0 |
| Control of Large Crabgrass | 31 | Example 2 + Oryzalin | 1.5 + 1.5 | 100.0 |
| | | | 1.0 + 1.5 | 100.0 |
| | | | 0.75 + 1.5 | 100.0 |
| | | Example 2 | 1.0 | 0 |
| | | Untreated Control | | 0 |
| Control of Morningglory | 31 | Example 2 + Oryzalin | 1.5 + 1.5 | 92.0 |
| | | | 1.0 + 1.5 | 90.0 |
| | | | 0.75 + 1.5 | 85.0 |
| | | Example 2 | 1.0 | 0 |
| | | Untreated Control | | 0 |
| Control of Common Purslane | 31 | Example 2 + Oryzalin | 1.5 + 1.5 | 100.0 |
| | | | 1.0 + 1.5 | 100.0 |
| | | | 0.75 + 1.5 | 100.0 |
| | | Example 2 | 1.0 | 98.8 |
| | | Untreated Control | | 0 |
| Control of Sida spp. | 31 | Example 2 + Oryzalin | 1.5 + 1.5 | 97.5 |
| | | | 1.0 + 1.5 | 96.3 |
| | | | 0.75 + 1.5 | 100.0 |
| | | Example 2 | 1.0 | 0 |
| | | Untreated Control | | 0 |

We claim:

1. A method for controlling undesired plants which comprises applying to the plants a growth inhibiting amount of a compound of the formula

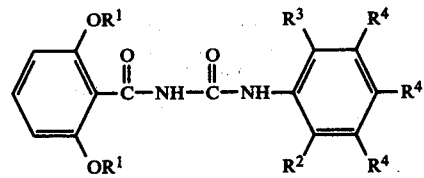

wherein both $R^1$ groups are the same and represent methyl; both $R^2$ and $R^3$ represent the same moiety which is methoxy or chlorine, and each $R^4$ represents hydrogen; or $R^2$ and $R^3$ both represent fluorine, and each $R^4$ independently represents hydrogen or fluorine.

2. The method of claim 1 in which the compound is 1-(2,6-dimethoxybenzoyl)-3-(2,6-dichlorophenyl)urea.

3. The method of claim 1 in which the compound is 1-(2,6-dimethoxybenzoyl)-3-(2,6-difluorophenyl)urea.

4. The method of claim 1 in which the compound is 1-(2,6-dimethoxybenzoyl)-3-(2,6-dimethoxyphenyl)urea.

5. The method of claim 1 in which the compound is 1-(2,6-dimethoxybenzoyl)-3-(2,4,6-trifluorophenyl)urea 6. The method of claim 1 in which the compound is 1-(2,6-dimethoxybenzoyl)-3-(2,3,5,6-tetrafluorophenyl)urea.

* * * * *